US012779198B2

(12) United States Patent
Theobald et al.

(10) Patent No.: US 12,779,198 B2
(45) Date of Patent: Nov. 3, 2026

(54) PERCUTANEOUS CIRCULATORY SUPPORT DEVICE WITH CANNULA AND EXPANDABLE ELEMENT

(71) Applicant: Boston Scientific Scimed Inc., Maple Grove, MN (US)

(72) Inventors: Cole Thomas Theobald, Mankato, MN (US); Brice Lee Shireman, Maple Grove, MN (US); Brian R. Reynolds, Ramsey, MN (US); Beth Camilleri, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 697 days.

(21) Appl. No.: 18/118,574

(22) Filed: Mar. 7, 2023

(65) Prior Publication Data

US 2023/0310829 A1 Oct. 5, 2023

Related U.S. Application Data

(60) Provisional application No. 63/317,732, filed on Mar. 8, 2022.

(51) Int. Cl.
*A61M 60/10* (2021.01)
*A61M 60/237* (2021.01)

(52) U.S. Cl.
CPC .......... *A61M 60/10* (2021.01); *A61M 60/237* (2021.01)

(58) Field of Classification Search
CPC ............................ A61M 60/10; A61M 60/237
See application file for complete search history.

(56) References Cited

U.S. PATENT DOCUMENTS 4,944,722 A 7/1990 Carriker et al.
5,295,958 A 3/1994 Shturman
5,370,618 A * 12/1994 Leonhardt ......... A61M 25/1034 604/103
5,527,159 A 6/1996 Bozeman, Jr. et al.
5,692,882 A 12/1997 Bozeman, Jr. et al.
(Continued)

FOREIGN PATENT DOCUMENTS

EP 847767 B1 2/2005
EP 2301598 B1 7/2017
(Continued)

OTHER PUBLICATIONS

US 9,067,007 B2, 06/2015, Tanner et al. (withdrawn)
(Continued)

*Primary Examiner* — Lindsey G Wehrheim
(74) *Attorney, Agent, or Firm* — Seager, Tufte & Wickhem LLP

(57) ABSTRACT

A percutaneous circulatory support device includes a housing comprising an inlet and an outlet, an impeller disposed within the housing and being rotatable relative to the housing to cause blood to flow into the inlet, through the housing, and out of the outlet, a cannula coupled to the housing, the cannula extending between a proximal section and a distal section opposite the proximal section, and an expandable element configured for inflation and deflation, the expandable element having a length that is approximately equal to a length of a body of the cannula. The expandable element is configured for providing an increased stiffness to the cannula.

20 Claims, 7 Drawing Sheets

(56) References Cited

U.S. PATENT DOCUMENTS

| | | | |
|---|---|---|---|
| 5,911,685 | A | 6/1999 | Siess et al. |
| 5,947,892 | A | 9/1999 | Benkowski et al. |
| 6,135,729 | A | 10/2000 | Aber |
| 6,139,487 | A | 10/2000 | Siess |
| 6,176,822 | B1 | 1/2001 | Nix et al. |
| 6,176,848 | B1 | 1/2001 | Rau et al. |
| 7,731,675 | B2 | 6/2010 | Aboul-Hosn et al. |
| 7,841,976 | B2 | 11/2010 | McBride et al. |
| 7,927,068 | B2 | 4/2011 | McBride et al. |
| 7,972,122 | B2 | 7/2011 | Larose et al. |
| 8,376,707 | B2 | 2/2013 | McBride et al. |
| 8,591,393 | B2 | 11/2013 | Walters et al. |
| 8,597,170 | B2 | 12/2013 | Walters et al. |
| 8,641,752 | B1 | 2/2014 | Holm et al. |
| 8,684,904 | B2 | 4/2014 | Campbell et al. |
| 8,721,517 | B2 | 5/2014 | Zeng et al. |
| 8,992,163 | B2 | 3/2015 | McBride et al. |
| 9,072,825 | B2 | 7/2015 | Pfeffer et al. |
| 9,138,518 | B2 | 9/2015 | Yuen et al. |
| 9,162,017 | B2 | 10/2015 | Evans et al. |
| 9,308,302 | B2 | 4/2016 | Zeng |
| 9,308,304 | B2 | 4/2016 | Peters et al. |
| 9,327,067 | B2 | 5/2016 | Zeng et al. |
| 9,364,592 | B2 | 6/2016 | McBride et al. |
| 9,364,593 | B2 | 6/2016 | McBride et al. |
| 9,381,288 | B2 | 7/2016 | Schenck et al. |
| 9,421,311 | B2 | 8/2016 | Tanner et al. |
| 9,446,179 | B2 | 9/2016 | Keenan et al. |
| 9,675,740 | B2 | 6/2017 | Zeng et al. |
| 9,717,833 | B2 | 8/2017 | McBride et al. |
| 9,770,543 | B2 | 9/2017 | Tanner et al. |
| 9,872,947 | B2 | 1/2018 | Keenan et al. |
| 9,895,476 | B2 | 2/2018 | Larose et al. |
| 9,907,890 | B2 | 3/2018 | Muller |
| 9,956,332 | B2 | 5/2018 | Larose et al. |
| 9,962,475 | B2 | 5/2018 | Yuen et al. |
| 9,964,115 | B2 | 5/2018 | Scheckel |
| 10,029,037 | B2 | 7/2018 | Muller et al. |
| 10,039,872 | B2 | 8/2018 | Zeng et al. |
| 10,071,192 | B2 | 9/2018 | Zeng |
| 10,086,121 | B2 | 10/2018 | Fitzgerald et al. |
| 10,105,475 | B2 | 10/2018 | Muller |
| 10,107,299 | B2 | 10/2018 | Scheckel |
| 10,117,980 | B2 | 11/2018 | Keenan et al. |
| 10,149,932 | B2 | 12/2018 | McBride et al. |
| 10,215,187 | B2 | 2/2019 | McBride et al. |
| 10,232,099 | B2 | 3/2019 | Peters et al. |
| 10,251,985 | B2 | 4/2019 | Larose et al. |
| 10,251,986 | B2 | 4/2019 | Larose et al. |
| 10,478,539 | B2 | 11/2019 | Pfeffer et al. |
| 10,478,540 | B2 | 11/2019 | Scheckel et al. |
| 10,525,178 | B2 | 1/2020 | Zeng |
| 10,576,192 | B2 | 3/2020 | Muller et al. |
| 10,576,193 | B2 | 3/2020 | Tanner et al. |
| 10,709,829 | B2 | 7/2020 | Muller |
| 10,709,830 | B2 | 7/2020 | Tanner et al. |
| 10,765,789 | B2 | 9/2020 | Zeng et al. |
| 10,780,208 | B2 | 9/2020 | Siess et al. |
| 10,786,610 | B2 | 9/2020 | Zeng |
| 10,799,624 | B2 | 10/2020 | Pfeffer et al. |
| 10,842,921 | B2 | 11/2020 | Siess et al. |
| 10,864,308 | B2 | 12/2020 | Muller et al. |
| 10,864,309 | B2 | 12/2020 | McBride et al. |
| 10,874,783 | B2 | 12/2020 | Pfeffer et al. |
| 10,894,115 | B2 | 1/2021 | Pfeffer et al. |
| 10,918,774 | B2 | 2/2021 | Stanfield et al. |
| 10,960,116 | B2 | 3/2021 | Yuen et al. |
| 10,980,927 | B2 | 4/2021 | Pfeffer et al. |
| 11,020,582 | B2 | 6/2021 | Cambronne et al. |
| 11,058,865 | B2 | 7/2021 | Fitzgerald et al. |
| 11,110,264 | B2 | 9/2021 | Cambronne et al. |
| 11,123,539 | B2 | 9/2021 | Pfeffer et al. |
| 11,129,978 | B2 | 9/2021 | Pfeffer et al. |
| 11,167,124 | B2 | 11/2021 | Pfeffer et al. |
| 11,227,986 | B2 | 1/2022 | Male et al. |
| 11,235,138 | B2 | 2/2022 | Gross-Hardt et al. |
| 11,253,693 | B2 | 2/2022 | Pfeffer et al. |
| 11,260,213 | B2 | 3/2022 | Zeng et al. |
| 11,273,301 | B2 | 3/2022 | Pfeffer et al. |
| 11,311,712 | B2 | 4/2022 | Zeng et al. |
| 11,338,214 | B2 | 5/2022 | White et al. |
| 11,357,967 | B2 | 6/2022 | Zeng et al. |
| 11,400,276 | B2 | 8/2022 | Chopra et al. |
| 11,497,896 | B2 | 11/2022 | Tanner et al. |
| 11,517,736 | B2 | 12/2022 | Earles et al. |
| 11,524,153 | B2 | 12/2022 | Alexander et al. |
| 11,583,659 | B2 | 2/2023 | Pfeffer et al. |
| 11,628,294 | B2 | 4/2023 | Chopra et al. |
| 11,666,747 | B2 | 6/2023 | Tuval et al. |
| 11,708,833 | B2 | 7/2023 | McBride et al. |
| 11,754,075 | B2 | 9/2023 | Schuelke et al. |
| 11,786,700 | B2 | 10/2023 | Pfeffer et al. |
| 11,813,445 | B2 | 11/2023 | Alexander et al. |
| 11,839,754 | B2 | 12/2023 | Tuval et al. |
| 2008/0114339 | A1 | 5/2008 | McBride et al. |
| 2008/0132747 | A1 | 6/2008 | Shifflette |
| 2008/0132748 | A1 | 6/2008 | Shifflette |
| 2008/0262337 | A1 | 10/2008 | Falwell et al. |
| 2009/0060743 | A1 | 3/2009 | McBride et al. |
| 2012/0041254 | A1 | 2/2012 | Scheckel |
| 2013/0303831 | A1 | 11/2013 | Evans |
| 2014/0107399 | A1 | 4/2014 | Spence |
| 2014/0200395 | A1 | 7/2014 | Shafi et al. |
| 2016/0096006 | A1 | 4/2016 | Cully et al. |
| 2016/0136343 | A1 | 5/2016 | Anagnostopoulos |
| 2017/0296725 | A1 | 10/2017 | Peters et al. |
| 2018/0126130 | A1* | 5/2018 | Nitzan ................. A61B 5/4878 |
| 2018/0303990 | A1 | 10/2018 | Siess et al. |
| 2018/0311423 | A1 | 11/2018 | Zeng et al. |
| 2019/0321530 | A1 | 10/2019 | Cambronne et al. |
| 2020/0155743 | A1 | 5/2020 | Siess et al. |
| 2020/0237981 | A1* | 7/2020 | Tuval .................... F04D 29/545 |
| 2020/0323670 | A1 | 10/2020 | Honeyfield et al. |
| 2021/0015982 | A1 | 1/2021 | Kerkhoffs et al. |
| 2021/0038785 | A1 | 2/2021 | Siess et al. |
| 2021/0106810 | A1 | 4/2021 | Pfeffer et al. |
| 2022/0134082 | A1 | 5/2022 | Pfeffer et al. |

FOREIGN PATENT DOCUMENTS

| | | | |
|---|---|---|---|
| EP | 3352808 | B1 | 9/2023 |
| WO | 2013025470 | A2 | 2/2013 |
| WO | 2013025470 | A3 | 2/2013 |
| WO | 2021119478 | A1 | 6/2021 |

OTHER PUBLICATIONS

International Search Report and Written Opinion for International Application No. PCT/US2023/014728, dated May 30, 2023. (32 pages).

* cited by examiner

PERCUTANEOUS CIRCULATORY SUPPORT DEVICE WITH CANNULA AND EXPANDABLE ELEMENT

CROSS-REFERENCE TO RELATED APPLICATIONS

This application claims priority to U.S. Provisional Application No. 63/317,732, filed Mar. 8, 2022, which is herein incorporated by reference in its entirety.

TECHNICAL FIELD

The present disclosure relates to percutaneous circulatory support devices. More specifically, the present disclosure relates to percutaneous circulatory support devices including a cannula with an expandable element.

BACKGROUND

Percutaneous circulatory support devices such as blood pumps can provide transient support for up to approximately several weeks in patients with compromised heart function or cardiac output. Several issues may complicate delivery and operation of blood pumps within the heart, including difficulty with guidewire advancement, trauma to cardiac tissue, and oscillation and/or migration of the blood pump resulting in decreased performance of the blood pump.

SUMMARY

In an Example 1, a percutaneous circulatory support device includes a housing, an impeller disposed within the housing and being rotatable relative to the housing, a cannula coupled to the housing, the cannula extending between a proximal section and a distal section opposite the proximal section, and an expandable element configured for inflation and deflation, the expandable element positioned around a body of the cannula. The expandable element is configured for providing an increased stiffness to the cannula.

In an Example 2, the device of Example 1 further includes wherein the expandable element has a length that is approximately equal to a length of the body of the cannula and an initial diameter and an inflated diameter, and wherein the inflated diameter is greater than the initial diameter.

In an Example 3, the device of Example 2 further includes wherein the expandable element has a length that is less than a length of the body of the cannula.

In an Example 4, the device of any one of Examples 1-3 further includes wherein the cannula comprises an outer diameter that is less than the inflated diameter and approximately equal to the initial diameter.

In an Example 5, the device of any one of Examples 1~4 further includes wherein expandable element is composed of silicone or an elastic polymer.

In an Example 6, the device of any one of Examples 1-5 further includes wherein when in an inflated configuration, the expandable element defines a lumen extending through the expandable element.

In an Example 7, the device of any one of Examples 1-6 further includes wherein the expandable element has a varying diameter along the length of the expandable element.

In an Example 8, the device of any one of Examples 1-7 further includes wherein when in an inflated configuration, the expandable element includes an outer inflated diameter and an inner inflated diameter.

In an Example 9, a percutaneous circulatory support device includes a housing, an impeller disposed within the housing and being rotatable relative to the housing to cause blood to flow through the housing, a cannula coupled to the housing and configured for receiving the blood that flows through the housing, the cannula having a body extending between a proximal section and a distal section opposite the proximal section, and an expandable element positioned around the body of the cannula, the expandable element extending a length that is approximately equal to a length of the body of the cannula. The expandable element is configured for providing an increased stiffness to the cannula.

In an Example 10, the device of Example 9 includes wherein the expandable element has an inflated configuration and a deflated configuration.

In an Example 11, the device of Example 10 includes wherein in the inflated configuration, the expandable element has an outer inflated diameter and an inner inflated diameter, and the inner inflated diameter defines a lumen extending through the expandable element.

In an Example 12, a method for positioning a blood pump within a subject, the blood pump including a cannula having a body extending between a proximal portion and a distal portion of the cannula, and the cannula having an expandable element positioned around the body of the cannula, and the expandable element having a length that is approximately equal to a length of the body of the cannula, includes advancing the blood pump through the vasculature of the subject, inflating the expandable element from an initial diameter to an inflated diameter, and crossing the aortic valve of the subject with the blood pump such that the cannula is positioned at least partially in the left ventricle of the subject.

In an Example 13, the method of Example 12 further includes wherein after inflation of the expandable element, the expandable element has an outer inflated diameter and an inner inflated diameter, the inner inflated diameter defining a lumen extending through the expandable element.

In an Example 14, the method of Example 12 or Example 13 further includes wherein the expandable element is a balloon comprised of silicone or an elastic polymer.

In an Example 15, the method of any one of Examples 12-14 further wherein the inflation of the expandable element increases a stiffness of the body of the cannula.

In an Example 16, a percutaneous circulatory support device includes a housing comprising an outlet, an impeller disposed within the housing and being rotatable relative to the housing to cause blood to flow through the housing and out of the outlet, a cannula coupled to the housing, the cannula extending between a proximal section and a distal section opposite the proximal section, and an expandable element configured for inflation and deflation, the expandable element having a length that is approximately equal to a length of a body of the cannula. The expandable element is configured for providing an increased stiffness to the cannula.

In an Example 17, the device of Example 16 further includes wherein the expandable element has an initial diameter and an inflated diameter.

In an Example 18, the device of Example 17 further includes wherein the inflated diameter is greater than the initial diameter.

In an Example 19, the device of Example 17 further includes wherein the cannula comprises an outer diameter that is less than the inflated diameter and approximately equal to the initial diameter.

In an Example 20, the device of Example 16 further includes wherein expandable element is composed of silicone or an elastic polymer.

In an Example 21, the device of Example 16 further includes when in an inflated configuration, the expandable element defines a lumen extending through the expandable element.

In an Example 22, the device of Example 16 further includes wherein the expandable element has a varying diameter along the length of the expandable element.

In an Example 23, the device of Example 16 further includes wherein when in an inflated configuration, the expandable element comprises an outer inflated diameter and an inner inflated diameter.

In an Example 24, the device of Example 23 further includes wherein the expandable element comprises a thickness defined as the distance between the outer inflated diameter and the inner inflated diameter.

In an Example 25, the device of Example 24 further includes wherein the thickness is approximately between 0.0005 inches and 0.020 inches.

In an Example 26, the device of Example 16 further includes wherein the expandable element has a generally circular cross section.

In an Example 27, the device of Example 16 further includes wherein the expandable element has a generally irregular shape cross section.

In an Example 28, a percutaneous circulatory support device includes a housing, an impeller disposed within the housing and being rotatable relative to the housing to cause blood to flow through the housing, a cannula coupled to the housing and configured for receiving the blood that flows through the housing, the cannula having a body extending between a proximal section and a distal section opposite the proximal section, and an expandable element positioned around the body of the cannula, the expandable element extending a length that is approximately equal to a length of the body of the cannula. The expandable element is configured for providing an increased stiffness to the cannula.

In an Example 29, the device of Example 28 includes wherein the expandable element has an inflated configuration and a deflated configuration.

In an Example 30, the device of Example 29 includes wherein in the inflated configuration, the expandable element has an outer inflated diameter and an inner inflated diameter, and the inner inflated diameter defining a lumen extending through the expandable element.

In an Example 31, a method for positioning a blood pump within a subject, the blood pump including a cannula having a body extending between a proximal portion and a distal portion of the cannula, and the cannula having an expandable element positioned around the body of the cannula, and the expandable element having a length that is approximately equal to a length of the body of the cannula, includes advancing the blood pump through the vasculature of the subject, inflating the expandable element from an initial diameter to an inflated diameter; and crossing the aortic valve of the subject with the blood pump such that the cannula is positioned at least partially in the left ventricle of the subject.

In an Example 32, the method of Example 31 further includes wherein after inflation of the expandable element, the expandable element has an outer inflated diameter and an inner inflated diameter, the inner inflated diameter defining a lumen extending through the expandable element.

In an Example 33, the method of Example 32 further includes wherein the outer inflated diameter has a value between approximately 2.00 and approximately 30.0 mm.

In an Example 34, the method of Example 31 further includes wherein the expandable element is a balloon comprised of silicone or an elastic polymer.

In an Example 35, the method of Example 31 further wherein the inflation of the expandable element increases a stiffness of the body of the cannula.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
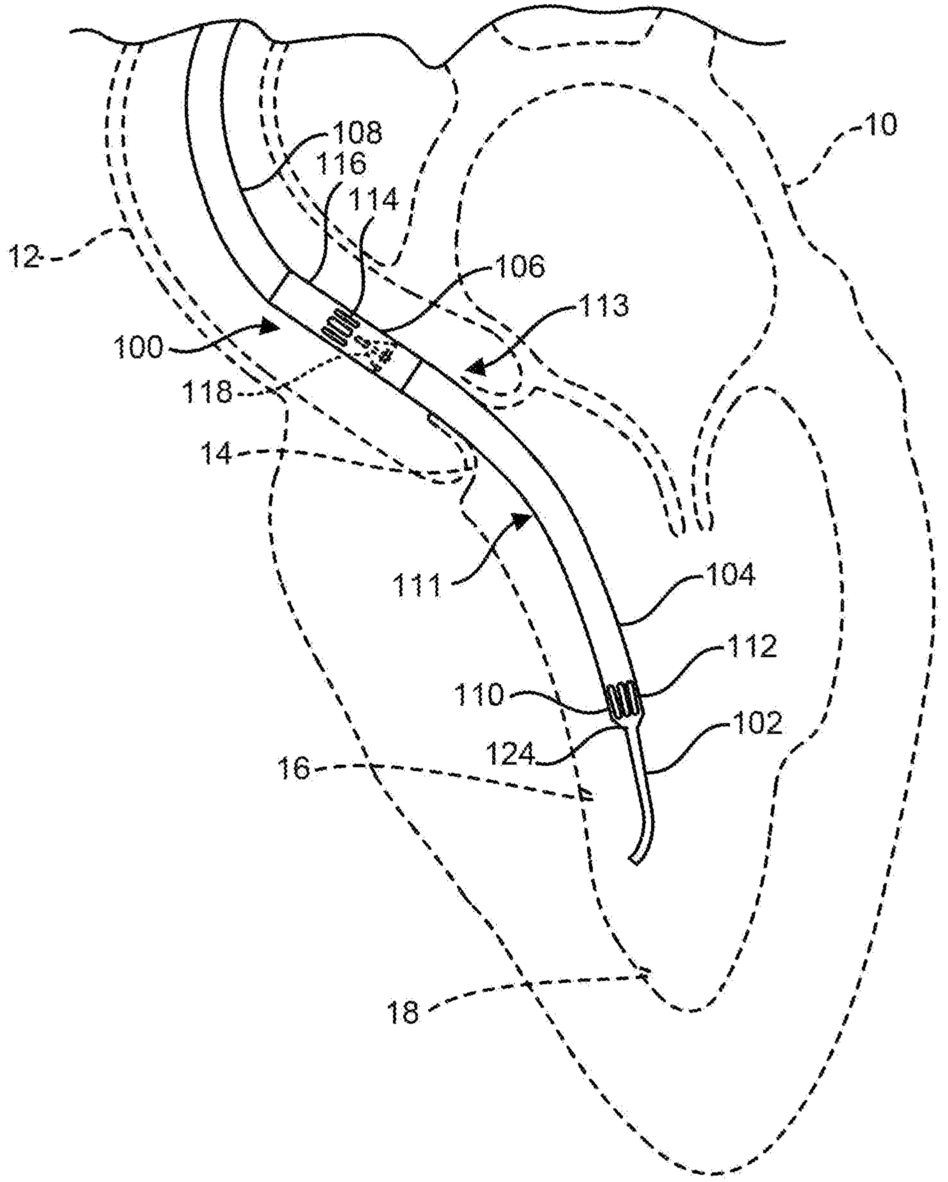
FIG. 1 illustrates a percutaneous circulatory support device after delivery into a patient's heart, in accordance with embodiments of the present disclosure.

FIG. 1 depicts a portion of an illustrative percutaneous mechanical circulatory support device 100 (also referred to herein, interchangeably, as a "blood pump"), and its relative position in a human heart 10, in accordance with embodiments of the subject matter disclosed herein. The blood pump 100 may be delivered percutaneously, through the vasculature and the aorta 12, and positioned within the heart 10 with respect to the aortic valve 14 and the left ventricle 16, as shown in FIG. 1. In some embodiments and as described in further detail below, the blood pump 100 may provide enhanced trackability and may be delivered without using an ancillary guidewire (not shown—that is, a guidewire separate from the blood pump 100). Alternatively, the blood pump 100 may be delivered using an ancillary guidewire.

With continued reference to FIG. 1, the blood pump 100 generally includes a distal tip portion 102, a cannula 104, an impeller portion 106, and a catheter 108. The cannula 104 may have a flexible construction to facilitate delivery of the blood pump 100. The cannula 104 includes one or more blood inlets 110 located on a distal portion 112 thereof, and one or more blood outlets 114 are located on a housing 116 of the impeller portion 106. A connector 124 may be positioned between the blood inlets 110 and the distal tip portion 102. The cannula 104 comprises a body 111 extending between the distal portion 112 and a proximal portion 113 of the cannula 104. More specifically, the distal portion 112 is positioned directly proximal to the inlets 110. The housing 116 carries an impeller 118, and the impeller 118 rotates relative to the housing 116 to cause blood to flow into the inlets 110, through the housing 116, and out of the outlets 114. During operation and as shown in FIG. 1, the blood pump 100 may be positioned within the heart 10 such that the inlets 110 are positioned in the left ventricle 16 and the outlets 114 are positioned in the aorta 12. As a result, rotation of the impeller 118 relative to the housing 116 causes blood to flow from the left ventricle 16, through the cannula 104 and the impeller portion 106, and into the aorta 12. In some cases, during operation the blood pump 100 may be positioned such that the distal tip portion 102 is located in close proximity of, or in contact with, the wall of the left ventricle 16, for example, in the location of the apex 18 of the left ventricle 16.

Figure 2A:
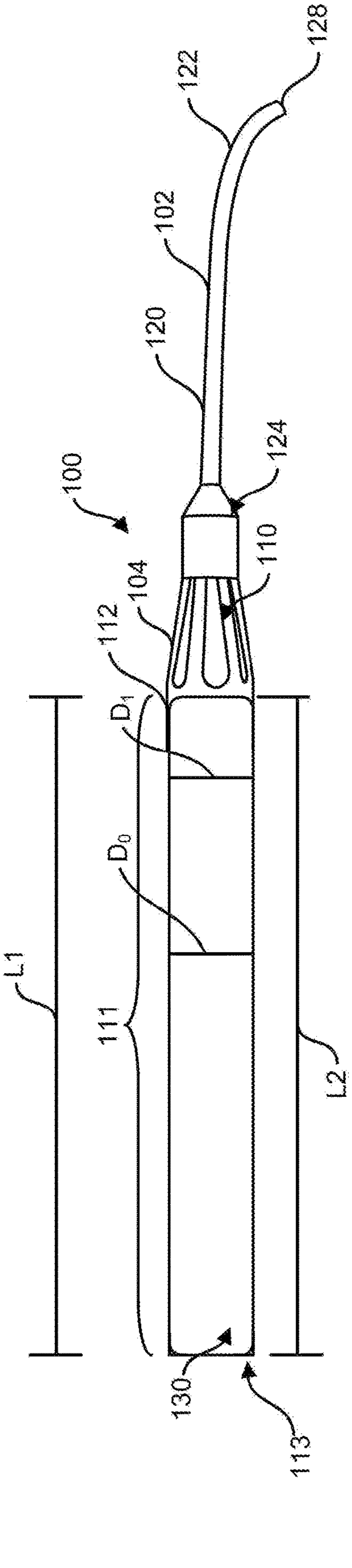
FIG. 2A illustrates a side view of a cannula and an expandable element in a first configuration, in accordance with embodiments of the present disclosure.
Figure 2B:
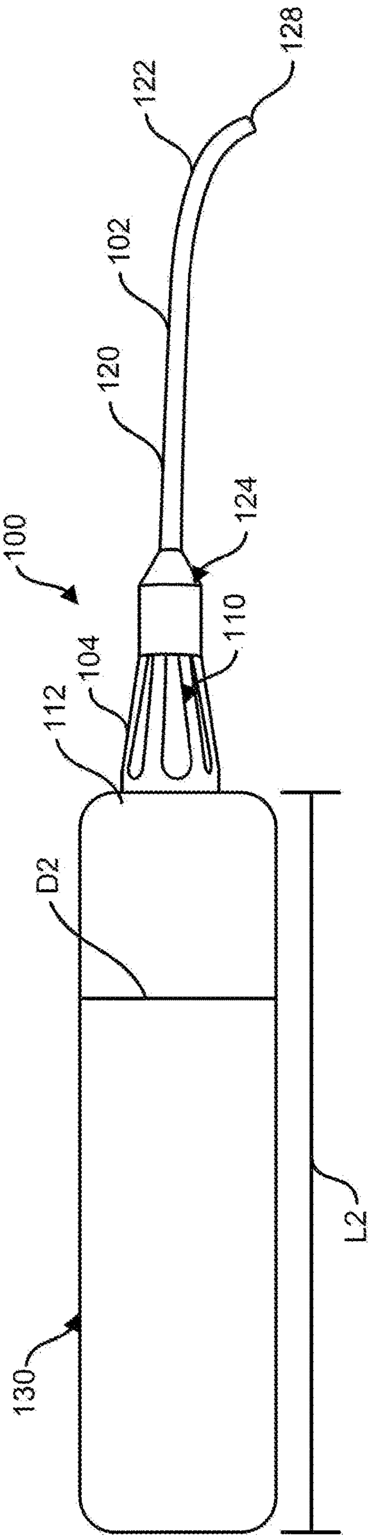
FIG. 2B illustrates a side view of the cannula and the expandable element of FIG. 1 in a second configuration, in accordance with embodiments of the present disclosure.

FIG. 2A illustrates a side view of the cannula 104. While the cannula 104 is illustrated as having the distal tip portion 102, in various embodiments, the distal tip portion 102 may be omitted from the cannula 104. Further, as illustrated, the cannula 104 includes an expandable element 130 positioned around the cannula 104 in a deflated configuration. The expandable element 130 may be positioned extending from the distal portion 112 to the proximal portion 113 of the cannula 104. In other words, the expandable element 130 is positioned on the body 111 of the cannula 104, and the body 111 of the cannula 104 has a length L1 extending between the distal portion 112 and the proximal portion 113. As illustrated, the expandable element 130 comprises a length L2 that may be approximately equal to the length L1 of the body 111 of the cannula 104. However, as will be described further with reference to FIG. 3, the length L2 of the expandable element 130 may be less than the length L1 of the body 111 of the cannula 104. In addition, as will be described further with reference to FIG. 4, the length L3 of the expandable element 130 may extend distally beyond the cannula 104. As illustrated in FIG. 2A, the expandable element 130 is positioned around the cannula 104 having a first, deflated diameter D1. The diameter D1 is approximately equal to an outer diameter Do of the cannula 104. The expandable element 130 may be configured to inflate, for example through operator manipulation or through self-expansion. For example, FIG. 2A illustrates the expandable element 130 in a deflated configuration and FIG. 2B illustrates a side view of the cannula 104 with the expandable element 130 in an inflated configuration. More specifically, in FIG. 2B, the expandable element 130 is illustrated having a second, inflated diameter D2. The second diameter D2 may be greater than the first diameter D1, and as such, the second diameter D2 may be greater than the outer diameter Do of the cannula 104.

Figure 2C:
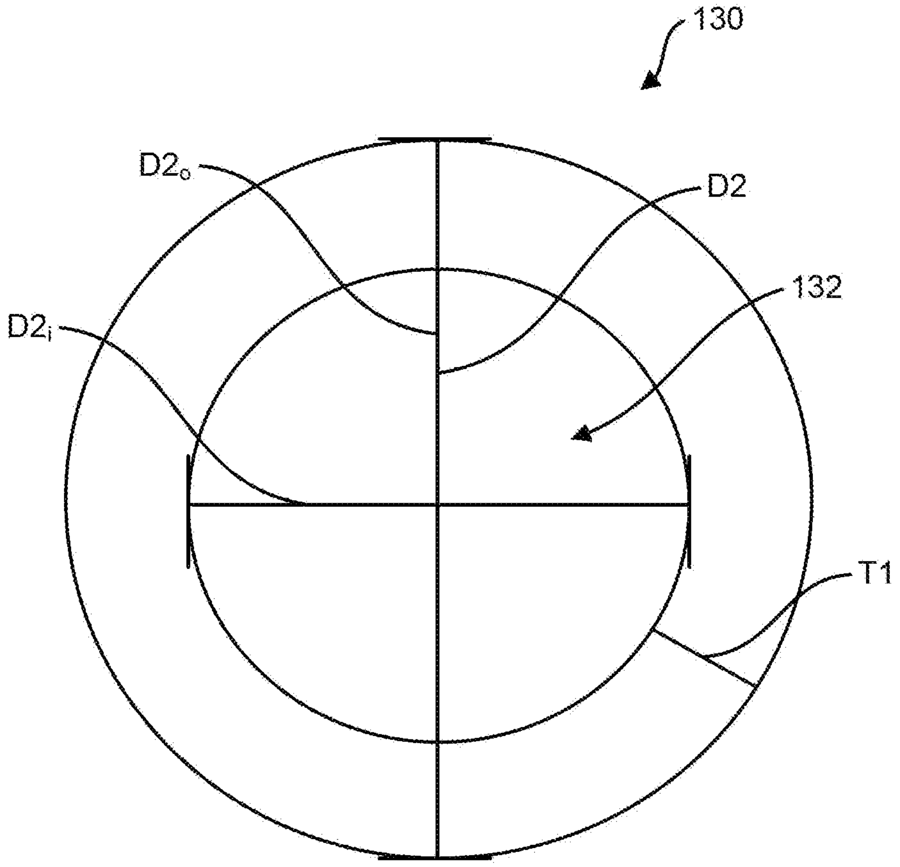
FIG. 2C illustrates a cross-sectional view of the expandable element of FIG. 2B, in accordance with embodiments of the present disclosure.

FIG. 2C illustrates a cross-sectional view of the expandable element 130 in the inflated configuration of FIG. 2B. As illustrated, in the inflated configuration, the expandable element 130 includes the inflated diameter D2. More specifically, the expandable element 130 comprises an outer inflated diameter D20 and inner inflated diameter $D\mathbf{2}_i$. The inner inflated diameter $D\mathbf{2}_i$ defines a lumen 132 extending through the expandable element 130. The lumen 132 is configured for receiving the body 111 of the cannula 104. While illustrated in FIGS. 2B and 2C as having a generally consistent outer inflated diameter $D\mathbf{2}_o$ and generally consistent inner inflated diameter $D\mathbf{2}_i$ throughout the length L2 of the expandable element 130, in some embodiments, the value of outer inflated diameter $D\mathbf{2}_o$ may vary along the length L2 of the expandable element 130. For example, the outer inflated diameter $D\mathbf{2}_o$ may have a larger value near the distal portion 112 of the cannula 104 and a smaller value near the proximal portion 113 of the cannula 104. In other embodiments, the outer inflated diameter $D\mathbf{2}_o$ may have a smaller value near the distal portion 112 of the cannula 104 and a larger value at the proximal portion 113 of the cannula 104. Additionally, in these embodiments, the inner inflated diameter $D\mathbf{2}_i$ may be generally constant along the length L2 of the expandable element 130, or, in other embodiments, the inner inflated diameter $D\mathbf{2}_i$ may vary along the length L2 of the expandable element 130. In some embodiments, the outer inflated diameter $D\mathbf{2}_o$ may have a value of between approximately 2.0 mm and 30 mm.

Additionally, as illustrated in FIG. 2C, the expandable element 130 comprises a thickness T1 that is defined as a distance between the inner inflated diameter D2; and the outer inflated diameter $D\mathbf{2}_o$. In some embodiments, the thickness T1 ranges between approximately 0.0005 inches to approximately 0.020 inches. In further embodiments, the thickness T1 ranges between 0.0005 inches and 0.005 inches. However, the value of the thickness T1 may vary and is not limited by the examples provided herein. Additionally, while the thickness T1 may be generally constant along the length L2 of the expandable element 130, in various embodiments the thickness T1 may vary along the length L2. For example, in embodiments wherein the outer inflated diameter $D\mathbf{2}_o$ varies along the length L2 of the expandable element 130 and the inner inflated diameter D2; maintains a constant value, the thickness T1 has a different value at the distal portion 112 than the value at the proximal portion 113.

In some embodiments, the expandable element 130 may be a balloon. Further, the expandable element 130 may be composed of silicone, a thermoplastic elastomer such as polyether block amide, polytetrafluoroethylene (PTFE), or another suitable elastic polymer. The material of the expandable element 130 may be chosen such that the expandable element 130 is capable of being repeatedly inflated and deflated without breaking or being damaged. Further, the expandable element 130 is configured for providing a stiffness to the cannula 104. In other words, inflation of the expandable element 130 along the cannula 104 may increase the overall stiffness of the cannula 104. In this way, the incorporation of the expandable element 130 may increase the trackability of the cannula 104 through the vasculature. This may additionally increase the ease with which a physician can steer and move the cannula 104 through the vasculature. For example, incorporation of the expandable element 130 may allow blood pump 100 to be delivered without using an ancillary guidewire. Additionally, the expandable element 130 may contribute to an atraumatic characterization of the cannula 104 and the blood pump 100. For example, as the cannula 104 is delivered into the vasculature of the subject, the expandable element 130 may come into contact with tissue of the vasculature and may have properties configured to reduce the damage that may occur to the tissue of the vasculature, in the event of contact. Also, as described in more detail below with respect to FIG. 4, the incorporation of the expandable element 130 may provide an atraumatic end portion to the cannula 104 and allow for the elimination of certain structures, such as distal tip portion 102, from the blood pump 100. Further, in some embodiments, steering technology may be inserted through or incorporated into the cannula 104 to manipulate the orientation of the expandable element 130 during delivery or operation. For example, the expandable element 130 may be manipulated using steering technology from the relatively linear configuration shown in FIG. 2B, to a generally curved configuration to aid in delivery or positioning of the cannula 104, and thus the blood pump 100.

Figure 3:
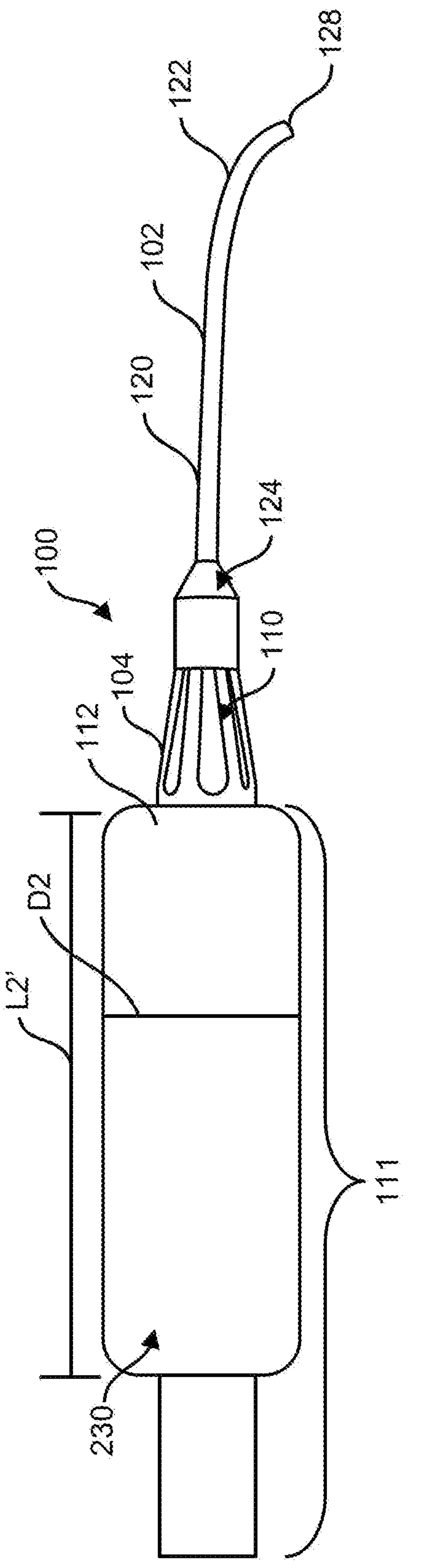
FIG. 3 illustrates a side view of a cannula and an expandable element, in accordance with embodiments of the present disclosure.

FIG. 3 illustrates an additional embodiment of the cannula 104 with an expandable element 230 positioned around the cannula 104. More specifically, the expandable element 230 is positioned around the body 111 of the cannula 104 and extends a length L2'. The length L2' has a value that is less than the value of the length L1 of the body 111 of the cannula 104. While illustrated positioned towards the distal portion 112 of the cannula 104, the expandable element 230 may be positioned at any position along the body 111 of the cannula 104. Additionally, the value of the length L2' may vary as well. For example, the length may be less than or greater than the length L2' shown in FIG. 3. In some embodiments, the position of the expandable element 230 along the cannula 104 may be adjusted by the physician for increased patient customization prior to use of the blood pump 100. The expandable element 230 additionally comprises a lumen (not shown) extending therethrough for receiving the cannula 104. The lumen of the expandable element 230 may be similar to the lumen 132 shown in FIG. 2C, however the lumen may have various other configurations.

Figure 4:
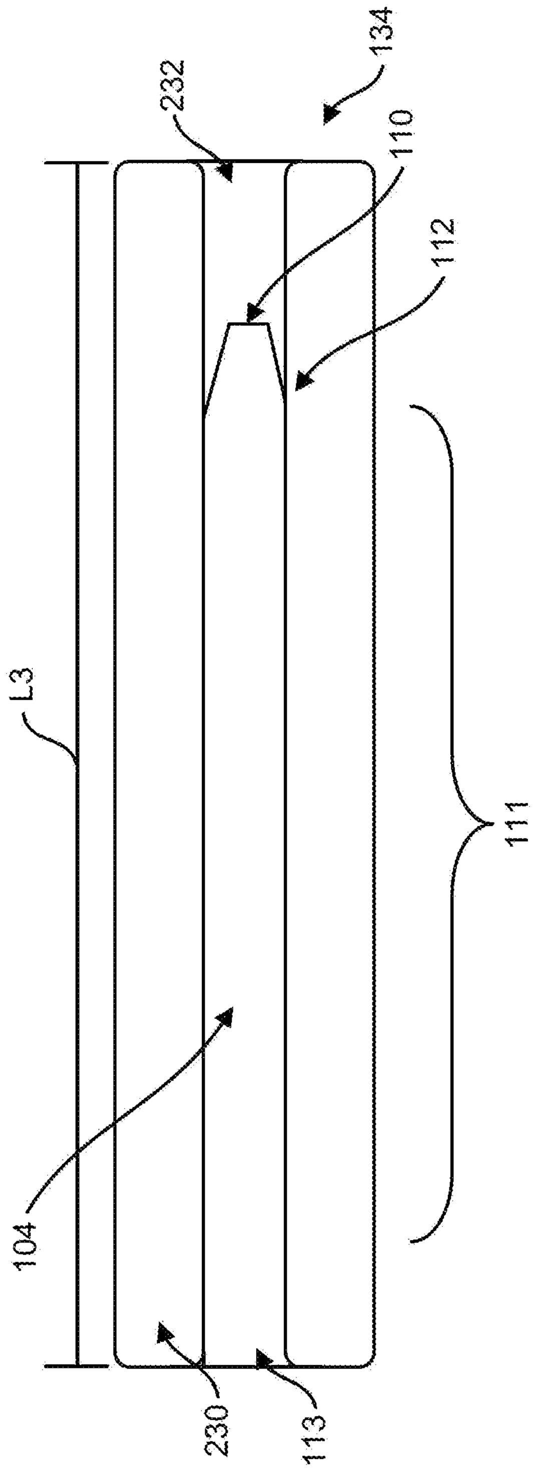
FIG. 4 illustrates a cross-sectional view of a cannula and an expandable element, in accordance with embodiments of the present disclosure.

FIG. 4 illustrates a cross-sectional view of the cannula 104 with an expandable element 230 positioned around the cannula 104. More specifically, the expandable element 230 is positioned around the body 111 of the cannula 104, and extends a length L3 such that the expandable element 230 extends beyond the distal portion 112 of cannula 104. The value of the length L3 may vary. For example, the length may be less than or greater than the length L3 shown in FIG. 4, and in particular, the expandable element 230 may not extend all the way to the proximal portion 113 of cannula 104. Additionally, in some embodiments the length L3 may be greater than the length of the cannula 104. In the embodiment of FIG. 4, the expandable element 230 extends beyond the distal portion 112 to form an atraumatic end 134 of cannula 104. In such an embodiment and as illustrated in FIG. 4, the distal tip portion 102 and connector 124 may be eliminated and the cannula 104 may include only one blood inlet 110. The expandable element 230 also comprises a lumen 232 extending therethrough for receiving the cannula 104. The lumen of the expandable element 230 may be similar to the lumen 132 shown in FIG. 2C, however the lumen may have various other configurations.

Figure 5C:
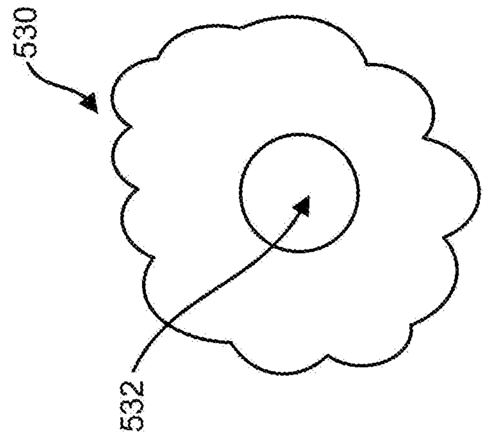
FIGS. 5A-5C illustrates various embodiments of an expandable element, in accordance with embodiments of the present disclosure.
Figure 5B:
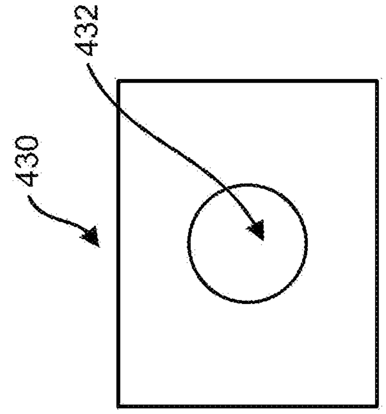
Figure 5A:
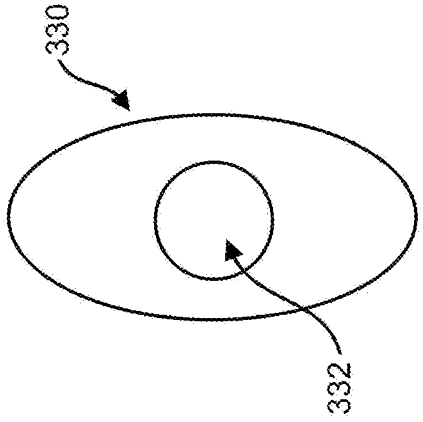

FIGS. 5A-5C illustrate various embodiments of an expandable element. For example, FIG. 5A illustrates a cross section of an expandable element 330 and a lumen 332 of the expandable element 330. In the illustrative embodiment of FIG. 5A, the cross section of the expandable element 330 is oval in shape. The lumen 332 of expandable element 330 is defined by a shape that is generally circular, which may aid in the ability to conform with the shape of the cannula 104 (FIG. 2). FIG. 5B illustrates a cross section of an additional embodiment of an expandable element 430. In the illustrative embodiment of FIG. 5B, the cross-sectional shape of the expandable element 430 is generally rectangular. As illustrated, a lumen 432 of the expandable element 430 has a generally circular shape, however, in various other embodiments the lumen 432 may be rectangular or otherwise irregular in shape. FIG. 5C illustrates a further example of an expandable element 530. Specifically, the cross-sectional shape of the expandable element 530 is generally irregular in shape, while the lumen 532 comprises a generally circular shape. However, the above-described examples are only provided as examples. Various other configurations of an expandable element may be provided in use with the blood pump 100, or various other percutaneous circulatory support devices.

Figure 6:
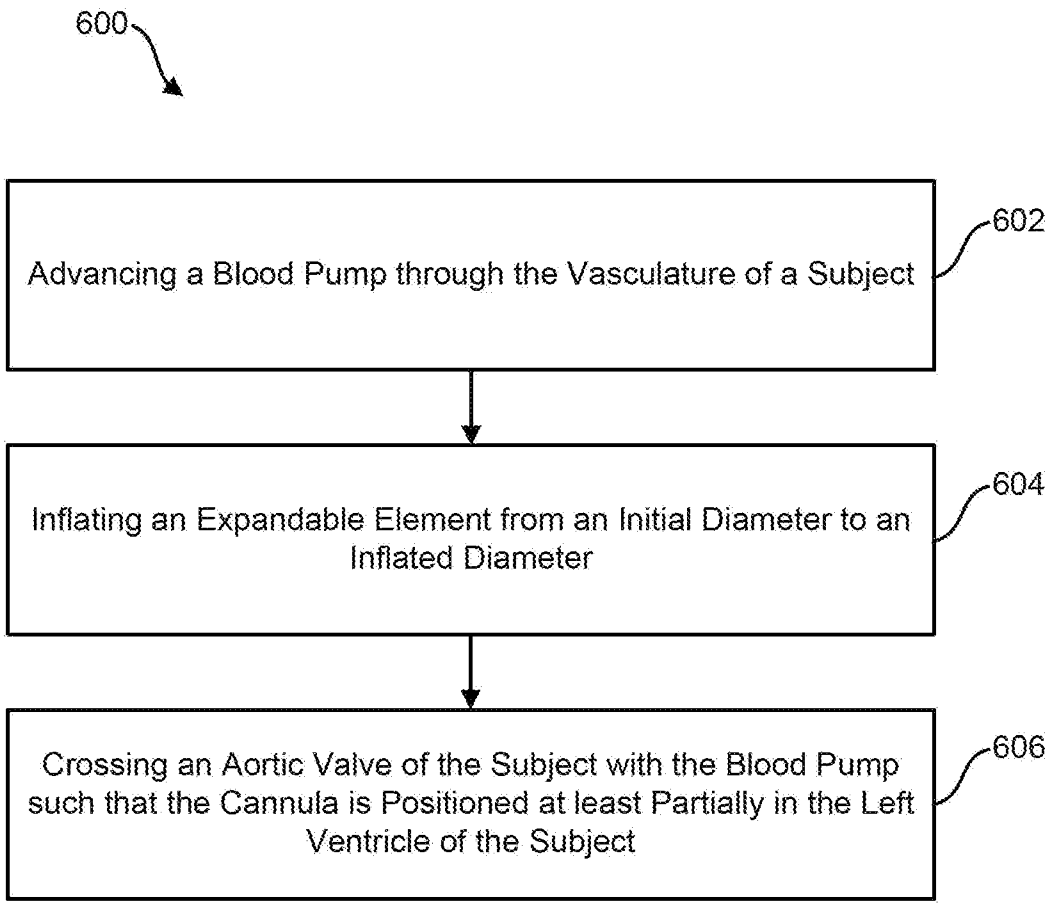
FIG. 6 illustrates a flow chart of a method for positioning a blood pump within a patient, in accordance with embodiments of the present disclosure.

With reference now to the flow chart of FIG. 6 and the embodiment as described with reference to FIGS. 1-2, a method 600 for positioning the blood pump 100 within a subject will be described further. At block 602, the method 600 first includes advancing the blood pump 100 into the vasculature of the subject. At block 604, the method 600 may then include inflating the expandable element 130 from the initial diameter D1 to the inflated diameter D2. As previously described, inflating the expandable element 130 may increase the stiffness of the cannula 104 to aid in trackability and control in steering of the cannula 104. In some embodiments, the inflation may be accomplished by the physician or the operator who is performing the procedure. For example, in some embodiments, the inflation is actuated through an actuator or other mechanism that is incorporated into the catheter 108 (FIG. 1) and available to the physician. However, various other inflation mechanisms may be incorporated. For example, the expandable element 130 may be self-expandable.

At block 606, the method 600 further includes crossing an aortic valve of the subject with the blood pump 100 such that the cannula 104 is positioned at least partially in the left ventricle of the subject. In various embodiments, the method 600 may further include the step of deflating the expandable element 130 after crossing the aortic valve with the blood pump 100. This may be desired for repositioning or removing the cannula 104. In other embodiments, the expandable element 130 may be deflated and subsequently inflated to an inflation diameter that is less than the inflated diameter D2, for example inflated to half of the inflation capacity.

While the method 600 is described with reference to the cannula 104 and the expandable element 130 as shown in FIG. 2, the cannula 104 and the method 600 may be used with any one of the expandable elements 230, 330, 430, 530 described herein.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. A percutaneous circulatory support device, comprising:

a housing comprising a blood outlet;

an impeller disposed within the housing and being rotatable relative to the housing to cause blood to flow through the housing and out of the outlet;

a cannula coupled to the housing, the cannula extending between a proximal section and a distal section opposite the proximal section;

a blood inlet positioned proximate the distal section, wherein the impeller is configured to convey blood flow through the cannula from the blood inlet to the blood outlet;

an expandable element configured for inflation and deflation, the expandable element having a length that is approximately equal to a length of a body of the cannula, the expandable element positioned proximal of the blood inlet; and wherein the expandable element is configured for providing an increased stiffness to the cannula.

2. The percutaneous circulatory support device of claim 1, further including wherein the expandable element has an initial diameter and an inflated diameter.

3. The percutaneous circulatory support device of claim 2, wherein the inflated diameter is greater than the initial diameter.

4. The percutaneous circulatory support device of claim 2, wherein the cannula comprises an outer diameter that is less than the inflated diameter and approximately equal to the initial diameter.

5. The percutaneous circulatory support device of claim 1, wherein the expandable element is composed of silicone or an elastic polymer.

6. The percutaneous circulatory support device of claim 1, wherein when in an inflated configuration, the expandable element defines a lumen extending through the expandable element.

7. The percutaneous circulatory support device of claim 1, wherein the expandable element has a varying diameter along the length of the expandable element.

8. The percutaneous circulatory support device of claim 1, wherein when in an inflated configuration, the expandable element comprises an outer inflated diameter and an inner inflated diameter.

9. The percutaneous circulatory support device of claim 8, wherein the expandable element comprises a thickness defined as the distance between the outer inflated diameter and the inner inflated diameter.

10. The percutaneous circulatory support device of claim 9, wherein the thickness is approximately between 0.0005 inches and 0.020 inches.

11. The percutaneous circulatory support device of claim 1, wherein the expandable element has a generally circular cross section.

12. The percutaneous circulatory support device of claim 1, wherein the expandable element has a generally irregular shape cross section.

13. A percutaneous circulatory support device, comprising:

a housing;

an impeller disposed within the housing and being rotatable relative to the housing to cause blood to flow through the housing;

a cannula coupled to the housing and extending distally from the housing, the cannula having a body extending between a proximal section and a distal section opposite the proximal section, the cannula including one or more blood inlets positioned at the distal section;

an expandable element positioned around the body of the cannula, the expandable element extending a length that is approximately equal to a length of the body of the cannula, wherein the expandable element is positioned proximal of the one or more blood inlets; and wherein the expandable element is configured for providing an increased stiffness to the cannula.

14. The percutaneous circulatory support device of claim 13, wherein the expandable element has an inflated configuration and a deflated configuration.

15. The percutaneous circulatory support device of claim 14, wherein in the inflated configuration, the expandable element has an outer inflated diameter and an inner inflated diameter, and the inner inflated diameter defining a lumen extending through the expandable element.

16. A method for positioning a blood pump within a subject, the blood pump comprising a housing with an impeller disposed within the housing, a cannula extending distally from the housing, the cannula having a body extending between a proximal section and a distal section of the cannula, the cannula including one or more blood inlets positioned at the distal section, and the cannula having an expandable element positioned around the body of the cannula proximal of the one or more blood inlets, and the expandable element having a length that is approximately equal to a length of the body of the cannula, the method comprising:

advancing the blood pump distally through the vasculature of the subject;

inflating the expandable element from an initial diameter to an inflated diameter; and crossing the aortic valve of the subject with the blood pump such that the distal section of the cannula is positioned at least partially in the left ventricle of the subject.

17. The method of claim 16, wherein after inflation of the expandable element, the expandable element has an outer inflated diameter and an inner inflated diameter, the inner inflated diameter defining a lumen extending through the expandable element.

18. The method of claim 17, wherein the outer inflated diameter has a value between approximately 2.0 mm and approximately 30 mm.

19. The method of claim 16, wherein the expandable element is a balloon comprised of silicone or an elastic polymer.

20. The method of claim 16, wherein the inflation of the expandable element increases a stiffness of the body of the cannula.

* * * * *